United States Patent [19]

Brennan et al.

[11] 4,269,783

[45] May 26, 1981

[54] CONVERSION OF SYNGAS TO HIGH OCTANE OLEFINIC NAPHTHA

[75] Inventors: James A. Brennan, Cherry Hill; Philip D. Caesar, Princeton; Julius Ciric, Pitman; William E. Garwood, Haddonfield; Robert E. Holland, Runnemede, all of N.J.

[73] Assignee: Mobil Oil Corporation, Fairfax, Va.

[21] Appl. No.: 775,129

[22] Filed: Mar. 7, 1977

[51] Int. Cl.$^3$ ............................................. C07C 27/06
[52] U.S. Cl. .................................. 518/718; 518/721; 518/712
[58] Field of Search ................ 260/449.6 R, 449.6 M

[56] References Cited
U.S. PATENT DOCUMENTS 2,588,511  3/1952  Friedman .......................... 260/449.6

Primary Examiner—Alan Siegel
Attorney, Agent, or Firm—Charles A. Huggett; Charles J. Speciale

[57] ABSTRACT

A method is disclosed for the conversion of a syngas to a liquid hydrocarbon product having a boiling range of less than 400° F. at a 90% overhead and being a predominantly olefinic product, wherein the olefins have substantially internal double bonds. The method for accomplishing this stated result involves an improvement in the method for the conversion of synthesis gas by contacting the same with a catalyst composite comprising a mixture of a Fischer-Tropsch catalyst and a volume excess of an acidic catalyst, e.g., silica-alumina or a crystalline aluminosilicate zeolite and wherein the activity of the acidic component is balanced with the activity of the Fischer-Tropsch component so as to maximize the yield of desired olefinic product.

6 Claims, No Drawings

CONVERSION OF SYNGAS TO HIGH OCTANE OLEFINIC NAPHTHA

BACKGROUND OF THE INVENTION

1. Field of the Invention

This invention is concerned with an improved process for converting synthesis gas, i.e. mixtures of gaseous carbon oxides with hydrogen or hydrogen donors, to hydrocarbon mixtures.

Processes for the conversion of coal and other hydrocarbons such as natural gas to a gaseous mixture consisting essentially of hydrogen and carbon monoxide and/or dioxide are well known. Those of major importance depend either on the partial combustion of the fuel with steam, or on a combination of these two reactions. An excellent summary of the art of gas manufacture, including synthesis gas, from solid and liquid fuels, is given in Encyclopedia of Chemical Technology, Edited by Kirk-Othmer, Second Edition, Volume 10, pages 353–433 (1966), Interscience Publishers, New York N.Y.

It is also well known that the synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

Recently, it has been discovered that the conversion of synthesis gas into valuable products can be greatly enhanced by employing a special type of crystalline aluminosilicate zeolite exemplified by ZSM-5 in admixture with conventional FischerTropsch catalyst. Thus, for example, in copending application Ser. No. 463,711, filed Apr. 24, 1974, there is disclosed a process for the conversion of syngas by passing the same at elevated temperature over a catalyst which comprises an intimate mixture of a Fischer-Tropsch component and a special type of zeolite such as ZSM-5. Said copending application points out that the products produced are hydrocarbon mixtures which are useful in the manufacture of heating oil, high octane gasoline, aromatic compounds, and chemical intermediates.

As can well be appreciated, the patent and technical literature relating to the Fischer-Tropsch process, is, indeed, extensive and the various catalysts reported in the prior art have been used by themselves as well as in admixture with catalytically inactive supports such as Kieselghur. Although the reasons for using catalytically inactive supports have varied, nevertheless, it would appear that one reason for using the same was that it resulted in increased surface area of the Fischer-Tropsch component upon which it was deposited or admixed and that is also aided in controlling the heat requirements of the overall exothermic reactions.

It is also known in the art to admix a Fischer-Tropsch component with a material, such as silica alumina which is known to be catalytically active for the conversion of hydrocarbons.

U.S. Pat. No. 2,637,739 discloses a Fischer-Tropsch process involving the conversion of syngas by passing the same over a Fischer-Tropsch catalyst in admixture with silica alumina.

U.S. Pat. No. 3,894,102 is directed towards a two-stage process for the conversion of syngas wherein in the first stage a methanol synthesis catalyst is admixed with an acidic dehydrogenation catalyst and the product thereof contacted with an HZSM-5 type zeolite.

The instant invention is concerned with the conversion of syngas over a catalyst comprising a Fischer-Tropsch component and an acidic cracking catalyst and is directed towards balancing the activity of the acidic component with the Fischer-Tropsch catalyst. The product obtained from the process of this invention is an olefinic product wherein the olefins have predominantly internal ($>50\%$) double bonds and the gasoline has a clear research octane number greater than 75. The solid acidic component utilized in the process of this invention is not a ZSM-5 type zeolite, but rather, it includes the use of an amorphous material, such as silica alumina, as well as the more conventional type crystalline aluminosilicate, such as faujasite, erionite, mordenite, etc. that are capable of sorbing n-hexane

2. Description of Preferred Embodiments

The novel process of this invention is directed towards an improvement in the process of converting syngas in that it is directed towards a process for the formation of a very specific product. The product with which the instant invention is concerned is a high octane predominantly olefinic naphtha having a boiling range of less than 400° F. at a 90% overhead which is defined as a $C_5+$ naphtha with an aromatic content of less than 15–20 weight percent and an olefin plus aromatics content exceeding 50% wherein the olefins have predominantly internal double bonds and the gasoline has a clear research octane number greater than 75. The instant invention is also concerned with obtaining the above-defined product in good yields and good selectivities from the starting syngas material.

It is believed that it is rather apparent that any time that a catalyst mixture is used of at least two components wherein each of said component performs a different catalytic function that the particular operating conditions at which the reaction is run does not necessarily optimize the catalytic function for both components. Thus, for example, in any given situation, the temperature at which a reaction is run might very well be a compromise between the optimum temperature for the Fischer-Tropsch component and the optimum temperature which is necessary for the acidic component.

It is well known in the Fischer-Tropsch art that specific Fischer-Tropsch catalyst vary in activity such that there are maximum temperatures at which specific Fischer-Tropsch catalyst can be used, otherwise an inordinate amount of methane and ethane will be formed.

However, in the majority of the heretofore carried out processes involving the Fischer-Tropsch reaction, the prior art workers were concerned with producing a particular product distribution and had to choose between the optimum condition for obtaining this product distribution and the excessive gas make which could accompany the desired reaction.

As has been previously set forth, this invention resides in the production of a particular product utilizing a catalyst mixture which can be a Fischer-Tropsch component and an acidic solid such as silica alumina. As is readily apparent from the admitted prior art, Applicants are not the first who have reacted syngas over such a catalyst composition, as is obvious from a consideration of U.S. Pat. No. 2,637,739, previously referred to. However, the previously practiced prior art processes simply did not utilize reaction conditions necessary to obtain the predominantly internal olefinic product to which this invention is directed.

It should be immediately understood that, as pointed out in the literature, a Fischer-Tropsch synthesis is an extremely complex reaction which is capable of producing different products at different operating conditions. Thus, for example, by way of generalization only, it has been reported in the literature that by operating at intermediate temperatures, i.e., 470°–650° F., at atmospheric pressure with bulk nickel and cobalt catalysts, methane is produced as the chief product. When an active form of iron, nickel or cobalt deposited on kieselguhr is used at low temperatures, i.e. 300°–400° F., higher hydrocarbon predominante which are almost wholly aliphatic and predominantly saturated. If the pressure is increased to 75–400 lbs psig and cobalt on kieselguhr is used as a catalyst, higher hydrocarbons, including some solid paraffins, are obtained. On the other hand, when iron is used at somewhat higher temperatures, olefins and paraffins are obtained and significant amounts of oxygenated compounds are also obtained, particularly at higher pressures and intermediate temperatures. If the temperature is further increased to 575°–675° F. and the pressure is increased to 225–600 lbs psig and an iron catalyst is used, the process can be carried out such as to yield a liquid hydrocarbon fraction which is chiefly olefinic and boils predominantly in the gasoline range. However, a significant fraction of oxygenates are also obtained. It is also known that by increasing the pressure to 1500–15,000 psig and lowering the temperature to 300°–400° F. and using ruthenium as a catalyst, higher molecular weight compounds are formed. Thus, from the above brief generalization, it can be seen that depending on numerous factors, such as catalyst, temperatures, pressures, space velocity, etc. that various products can be obtained in the conversion of syngas.

While not wishing to be bound by any theory of operation, nevertheless, it appears that in the novel process of this invention, all that is required from the Fischer-Tropsch portion of the catalyst is that it be capable of converting the syngas to an olefinic product at a minimum temperature of at least 520° F. and more desirably, at least 600° F. up to a maximum temperature of 800° F. such that no more than about 30 weight percent of methane plus ethane is formed.

The acidic component has one or more functions. One is to intercept α-olefin intermediates, such as 1-butene and 1-pentene, and convert them to 2-butene and 2-pentene. This helps retard further build-up of high molecular weight waxy olefins on subsequent contact with Fischer-Tropsch catalyst sites which poisons and deactivates the sites. Another function is to crack heavier olefins to keep the product within the gasoline range. These functions, depending on the activity of the acidic component occur at a minimum temperature of at least 520° F. and more desirably, at least 600° F.

Thus, it can be seen that the novel process of this invention does not have the same constraints with respect to the use of Fischer-Tropsch catalyst as existed in heretofore practiced prior art processes. The entire function of the Fischer-Tropsch catalyst in the novel catalyst combination of this invention is merely to produce olefinic hydrocarbon intermediates from syngas at good yields and good selectivity, but the particular nature of the olefinic hydrocarbons produced really does not matter too much, since the acidic solid can act on this olefinic product and transform it to the particular olefinic gasoline with which the novel process of this invention is concerned. Thus, all that is required with respect to the Fischer-Tropsch component is that one be picked that will carry out the conversion of syngas at a temperature higher than 500° F. but not higher than 800° F., such that no more than about 30 weight percent of methane plus ethane is formed.

Although there are many factors which can be taken into consideration when one is discussing the severity of a reaction, nevertheless, by far the most important parameter is the temperature. Thus, once a particular Fischer-Tropsch catalyst is chosen to meet the above set forth criterion, the temperature of the reaction is already fixed. Although the particular temperature will vary depending upon the particular Fischer-Tropsch catalyst component which is employed, the simple fact remains that for any given Fischer-Tropsch component, the specific temperature which will cause syngas to react to form an olefinic product and produce no more than about 30 weight percent of methane plus ethane is easily determined.

It then becomes necessary, in the course of the novel process of this invention to balance the activity of the acidic solid component utilized in the catalyst composition, such that it will be able to function at the preset temperature determined by the Fischer-Tropsch component and produce the desired products. It is known in the art that the activity of a zeolite varies, depending upon the particular cationic substitution, as well as by its silica to alumina ratio, whether or not it has been steamed, etc. Another way of reducing the activity of the zeolite is to dilute it with inorganic type materials, such as alumina, silica-alumina, clay, etc. This has the effect of increasing the space velocity of the feed with respect to the zeolitic component such that the severity of the reaction is reduced. Conversely, the activity of the zeolite can be increased by increasing the volume ratio of acidic component with respect to the Fischer-Tropsch component. This, in effect, lowers the space velocity of the feed with respect to the zeolitic component. It also increases the probability that light α-olefin intermediates will be intercepted by the zeolite and converted to internal olefins.

As can be seen from the description of the process of this invention, the most conventionally used method for modifying the activity of any given zeolite, i.e. the temperature, cannot be effectively utilized in the instant process. As has hertofore been stated, the temperature of the operation is predetermined or preset by the particular Fischer-Tropsch component utilized and the acidic solid must be made to function within that temperature in order to obtain the desired products.

In this connection, it is known in the art that, in general, the activity of a crystalline aluminosilicate zeolite is greater than the activity of an amorphous type material, such as silica alumina. However, it is also known in the art that the activity of the crystalline aluminosilicate zeolite varies depending on the particular cationic substitution and in this connection, it has been found that the crystalline aluminosilicate zeolite employed in the novel process of this invention must be used in the hydrogen form, i.e., a substantial portion of the cations originally associated therewith must be replaced with hydrogen ions or ammonium ions such that the zeolite has a substantial catalytic activity. As is known in the art, alkali metal cations, such as sodium ions, are detrimental to the catalytic activity of a zeolite, and in this connection, the zeolites utilized can have no more than one half weight percent and more preferably <0.1 weight percent of alkali metal cations associated therewith. It is to be understood that the cations originally associated with the zeolites can also be replaced by rare earth cations or mixtures of rare earth cations, hydrogen, or ammonium ions. As previously pointed out, it is preferred to use the zeolites in their hydrogen form.

On the other hand, when the acidic solid utilized with the Fischer-Tropsch component in an amorphous solid, such as silica alumina or silica magnesia, its inherent catalytic activity is simply not great enough for it to be effectively utilized at the low temperature ranges of this process. Thus, silica alumina will only perform the type of chemistry which is necessary to yield the desired product in accordance with the teachings of this invention at a substantially higher temperature, and, in this connection, can only be effectively utilized at temperatures of at least 550° F., and more preferably at temperatures ranging from 600° to 800° F. However, it must be immediately realized that the novel process of this invention does not merely involve the use of a Fischer-Tropsch component and an acidic solid over any range of operating conditions, but does have for its essential requirement that the activity of the acidic solid be balanced with the activity of the Fischer-Tropsch component such that the olefinic product of this invention will be obtained.

By way of illustrating the absolute necessity of balancing the activity of the solid acidic component with the particular Fischer-Tropsch component in order to obtain the maximum yield of the particular product, the following general principles can be applied.

It is known that the catalytic activity of various Fischer-Tropsch components is different and, in general, it can be stated that the art has recognized that ruthenium is more active than iron. Another way of stating the same thing is that usually it would require a lower temperature to convert syngas with a ruthenium catalyst than it would with an iron catalyst under the same conditions. If a ruthenium catalyst were employed which would convert syngas and produce no more than about 30 weight percent methane plus ethane at about 500° F., it would not be possible to use silica alumina as the acidic solid; the reason being that the catalytic activity of silica-alumina is simply too small to adequately function at these low temperatures to give the type of conversion necessary to produce the particular olefinic product. Thus, silica-alumina can only be used at temperatures of about 600° F. and, in general, it is preferred to use iron catalysts when utilizing silica-alumina.

On the other hand, the hydrogen form of crystalline aluminosilicates can be used throughout the entire temperature range of this invention, but at the upper ends of the temperature range, it might very well be necessary to dilute the crystalline aluminosilicate zeolite with an amorphous material such as silica-alumina, alumina, silica gel, or any other inorganic oxide.

As has heretofore been stated, the novel process of this invention is carried out at temperatures ranging from about 500° and more preferably at least 600° F. to about 800° F. The novel process of this invention is carried out at gas hourly space velocities (GHSV) ranging from 500 to 30,000, and more desirably from 1000 to 10,000. Hydrogen to CO ratios can vary from 0.5 to 6.0 and more preferably from 1.0 to 3.0, pressures ranging from 100 to 1000 psig and more preferably from 100 to 400 psig. The ratio of the Fischer-Tropsch component to the acidic solid can range from a minimum of 1.0 to a functional maximum of 20.0 volumes of the acidic solid per volume of the Fischer-Tropsch component. A particularly desirable range is from 2 to 10 volumes of acidic solid per volume of Fischer-Tropsch component.

Operating within the above-referred-to parameters will result in a process wherein over 50% of one or both of the fresh freed reactants, carbon monoxide, and hydrogen is converted.

The following examples will illustrate the best mode now contemplated for carrying out the invention.

EXAMPLES 1-4

Syngas was contacted at a temperature of 630° F., a pressure of 200 psig and a space velocity of 3000 GHSV, a hydrogen to carbon monoxide ratio of 2 with various catalysts in order to study their effect on a Fischer-Tropsch synthesis. In each case, separate particles of the particular solid and separate particles of potassium promoted iron, Fe(K), were employed. In each case, the volume ratio of the solid to the potassium promoted iron was 4:1.

The results were as follows:

TABLE

| Example | 1 | 2 | 3 | 4 |
|---|---|---|---|---|
| Separate Particles of Fe(K) + | γ-Al$_2$O$_3$ | H-Hrionite | 46 Al Beads | TEA Mordenite |
| CO Conversion, wt % | 96 | 96 | 95 | 96 |
| C$_5$ Composition, wt % | | | | |
| Olefins | 84 | 83 | 84 | 83 |
| 1-Pentene | 70 | 14 | 12 | 8 |
| 2-Pentenes | 12 | 61 | 60 | 61 |
| Methylbutenes | 18 | 25 | 18 | 31 |
| Products | | | | |
| C$_1$ + C$_2$, wt % | 23 | 28 | 24 | 31 |
| C$_5$ + Liquid, wt % | 50 | 42 | 49 | 41 |
| R + O | 60-65 est. | 82 | 82 | 82 est. |
| Arom. + Olef., wt % | 85 | 83 | 85 | 84 |
| 90% OH at °F. | 480 | 370 | 370 | 350 |

As can be seen from the above examples, hydrogen erionite, silica-alumina, and TEA Mordenite all perform so as to give the desired product. On the other hand, alumina resulted in the production of a product which had too low an octane number and whose 90% overhead point was also too high. Reference to said table will also show that the use of alpha alumina resulted in the product of C$_5$ olefins predominating in 1-pentene, rather than producing a product wherein the olefins had predominately internal double bonds.

EXAMPLES 5-7

Syngas was contacted at a temperature of 630° F., a pressure of 200 psig and a space velocity of 3000 GHSV, a hydrogen to carbon monoxide ratio of 2 with HZSM-4 and with REY to determine the effect of sodium and/or potassium on the activity of the zeolite in the Fischer-Tropsch synthesis. In each case, separate particles of the particular solid and separate particles of potassium iron were employed. In each case, the volume ratio of acidic solid to the potassium iron was 4:1.

The results were as follows:

TABLE

| Example | 5 | 6 | 7 |
|---|---|---|---|
| Separate Particles of Fe(K) + | REY | HZSM-4 | HZSM-4 |
| Na, wt % | 3.4 | 1.01 | 0.03 |
| CO Conversion, wt % | 98 | 97.5 | 99 |
| $C_5$ Composition, wt % | | | |
| Olefins | 80 | 82 | 84 |
| 1-Pentene | 60 | 28 | 11 |
| 2-Pentene | 22 | 51 | 50 |
| Methylbutenes | 18 | 21 | 39 |
| Products | | | |
| $C_1 + C_2$, wt % | 33 | 29 | 33 |
| $C_5$ + Liquid, wt % | 38 | 42 | 36 |
| Arom. + Olef. wt % | 81 | 83 | 85 |
| 90% OH at °F. | 440 | 450 | 380 |

As can be seen from the above examples, 0.1% or more of sodium in the HZSM-4 or REY resulted in the production of products of higher boiling range than naphtha. Reference to said table will also show that the production of low octane α-olefins was undesirably high as indicated by 1-pentene in the $C_5$ fraction. It can also be seen that both the 90% overhead and 1-pentene content were reduced to the desired levels by reducing the sodium content of the HZSM-4 to 0.05%.

EXAMPLE 8

Syngas was contacted at a temperature of 518° F., a pressure of 200 psig, 1300 GHSV, and a hydrogen to carbon monoxide ratio of 1 with H-erionite of the same composition as that in Example 2 mixed with separate particles of 20% cobalt precipitated on a silica-zirconia-clay base. The volume ratio of H-erionite particles to cobalt-containing particles was 2.3:1.

As can be seen from the following table, the product had too high a boiling range even though the olefins made had substantially internal double bonds. The activity of the acidic component at the temperature and space velocity chosen was not sufficiently great enough to produce the desire product. Although lowering the space velocity would result in a lower boiling range product, it appears that 520° F. is the lowest practical operating temperature.

TABLE

| Example | 8 |
|---|---|
| CO Conversion, wt % | 27 (54% theoretical) |
| $H_2$ Conversion, wt % | 53 |
| wt % C converted to $CO_2$ | 1 |
| Hydrocarbon | 99 |
| Hydrocarbon Composition, wt % | |
| $C_1 + C_2$ | 22 |
| $C_3 + C_4$ | 16 |
| $C_5 +$ | 62 |
| $C_5$ Fraction, wt % | |
| Olefins | 66 |
| 1-pentene | 9 |
| 2-pentenes | 59 |
| Methylbutenes | 32 |
| Liquid Product - 90% OH at °F. | 500 |

EXAMPLE 9

Syngas was contacted at a temperature of 600° F., a pressure of 200 psig, 3000 GHSV, and a hydrogen to carbon monoxide ratio of 2 with H-erionite mixed with separate particles of FeK. The volume ratio of H-erionite particles to FeK was 1.0. The results of this run are compared in the following table with those of Example 2, in which the volume ratio was 4.0.

Note particularly the higher alpha-olefin content, higher boiling range and greater rate of catalyst deactivation associated with the low ratio catalyst.

TABLE

| Example | 9 | | 2 | |
|---|---|---|---|---|
| Vol. Ratio, H-Erionite/Fe(K) | 1.0 | | 4.0 | |
| Accumulated Time, Days | 2 | 3 | 2 | 3 |
| CO Conversion, wt % | 81 | 46 | 96 | 96 |
| $H_2$ Conversion, wt % | 40 | 29 | 54 | 54 |
| wt % C converted to $CO_2$ | 32 | 33 | 30 | 31 |
| Hydrocarbon | 68 | 67 | 70 | 69 |
| Hydrocarbon Composition, wt % | | | | |
| $C_1 + C_2$ | 18 | 18 | 28 | 28 |
| $C_3 + C_4$ | 25 | 22 | 30 | 30 |
| $C_5 +$ | 57 | 60 | 42 | 42 |
| $C_5$ Fraction, wt % | | | | |
| Olefins | 88 | 78 | 85 | 83 |
| 1-pentene | 25 | 41 | 12 | 14 |
| 2-pentenes | 54 | 39 | 60 | 61 |
| Methylbutenes | 21 | 20 | 28 | 25 |
| Liquid Product - 90% OH at °F. | 500 | 565 | 370 | 370 |

What is claimed is:

1. In a syngas conversion process wherein a mixture of gaseous carbon oxides and hydrogen at hydrogen donors is contacted at elevated temperatures and pressures with a Fischer-Tropsch catalyst, the improvement which comprises carrying out said conversion at a temperature of from 500° to 800° F., a space velocity of from 1000 to 30,000 GHSV, and a pressure of from 100 to 1000 psig with a catalyst composite comprised of an intimate mixture of an iron Fischer-Tropsch component and a component containing an acidic solid wherein the volume ratio of said component containing an acidic solid to said iron Fischer-Tropsch component is 1-20, said acidic solid being selected from the group consisting of hydrogen exchanged silica-alumina, silica-magnesia, erionite, mordenite, faujasite, and ZSM-4 with the proviso that when the acidic solid is silica-alumina or silica-magnesia, the temperature is at least 600° F., and with the further proviso that when the acidic solid is a zeolite, the zeolite has no more than 0.5 wt.% of alkali metal cations associated therewith, and recovering a product comprising an olefinic naphtha having a boiling range of less than 400° F. at 90% overhead with an aromatic content less than 20 weight percent, an olefin plus aromatic content of at least 50 weight wherein the olefins have predominantly internal double bonds.

2. The process of claim 1, wherein the volume ratio of acidic solid to iron is 2-10.

3. The process of claim 1 wherein the acidic solid is hydrogen exchanged erionite.

4. The process of claim 1 wherein the acidic solid is hydrogen exchanged mordenite.

5. The process of claim 1 wherein the acidic solid is hydrogen exchanged faujasite.

6. The process of claim 1 wherein the acidic solid is hydrogen exchanged ZSM-4.

* * * * *

UNITED STATES PATENT AND TRADEMARK OFFICE
CERTIFICATE OF CORRECTION

PATENT NO. : 4,269,783

DATED : May 26, 1981

INVENTOR(S) : James A. Brennan et al.

It is certified that error appears in the above—identified patent and that said Letters Patent is hereby corrected as shown below:

Claim 1, line 2, Column 8, line 28, "at" should read -- or --.

Signed and Sealed this

Nineteenth Day of January 1982

[SEAL]

Attest:

Attesting Officer

GERALD J. MOSSINGHOFF

Commissioner of Patents and Trademarks